United States Patent [19]

Zaias

[11] Patent Number: 5,059,192

[45] Date of Patent: Oct. 22, 1991

[54] METHOD OF HAIR DEPILATION

[76] Inventor: Nardo Zaias, 36 Star Island, Miami Beach, Fla. 33139

[21] Appl. No.: 513,850

[22] Filed: Apr. 24, 1990

[51] Int. Cl.$^5$ .............................................. A61N 5/00
[52] U.S. Cl. ....................................................... 606/9
[58] Field of Search ............... 606/9, 16, 43; 128/398, 128/395

[56] References Cited

U.S. PATENT DOCUMENTS

| | | | |
|---|---|---|---|
| 3,538,919 | 11/1970 | Meyer | 128/398 |
| 3,834,391 | 9/1974 | Block | 606/9 |
| 4,174,714 | 11/1979 | Mehl | 606/43 |
| 4,388,924 | 6/1983 | Weissman et al. | 606/17 |

OTHER PUBLICATIONS

"Pigmented Guinea Pig Skin Irradiated with Q-S-witched Ruby Laser Pulses", Arch Dermatol, 125:43–49, 1989.

"Effect of Wavelength on Cutaneous Pigment Using Pulsed Irradiation", J I Invest Dermatol, 92:717–720, 1989.

*Primary Examiner*—Lee S. Cohen
*Attorney, Agent, or Firm*—Shlesinger Arkwright & Garvey

[57] ABSTRACT

A method of depilation using a ruby red laser includes supplying optimum energy to a selected area of skin to cause follicular injury to the extent that depilation occurs without epidermal scaring.

6 Claims, 1 Drawing Sheet

METHOD OF HAIR DEPILATION

FIELD OF THE INVENTION

This invention relates to a method of hair depilation involving treatment of a single hair or a group of hairs simultaneously with a ruby red laser.

BACKGROUND OF THE INVENTION

Treatment of skin with lasers have been the subject of study since the early 1960s. A variety of lasers have been used in dermatologic practice. Different lasers are primarily distinguished by the wavelength of the light produced, measured in nanometers, such as the XeF excimer (351 nm), argon (488 nm, 514 nm), ruby (694 nm), Nd:YAG(1060 nm), and $CO_2$ (10,600 nm) lasers.

More recently, photothermolysis of skin has been demonstrated using xenon fluoride (XeF) laser pulses and Q-switched ruby laser pulses. It has been found that radiation from Q-switched ruby lasers deeply penetrates the epidermis. It has also been found that application of ruby red laser energy can cause depigmentation of the skin as well as significant follicular damage to the extent that the hair will fall out.

Up to now, the Q-switched ruby laser has been used for the treatment of tattoos and conventional ruby lasers have been used to treat epidermal and dermal pigmented lesions. Studies based on experimentation with Q-switched ruby lasers, as well as other lasers, have reported skin depigmentation and temporary hair loss. Two particular studies titled "Pigmented Guinea Pig Skin Irradiated With Q-switched Ruby Laser Pulses", *Arch Dermatol*, 125:43–49, 1989 and "Effect of Wavelength on Cutaneous Pigment Using Pulsed Irradiation", *J Invest Dermatol*, 92:717–720, 1989, teach depigmentation generally and discuss hair regrowth, but do not deal specifically with permanent substantial hair removal. The intent of these studies was not to damage the follicle or the papilla such that the hair would be subject to a disruption of the normal growing cycle over an extended period of time or permanently destroyed.

OBJECTS AND SUMMARY OF THE INVENTION

It is an object of the this invention to provide a method for depilation of hair and prevention of regrowth using a ruby red laser.

Another object of the invention is to provide a method for treating either a single or a group of hairs simultaneously.

Still another object of the invention is to provide a method of hair removal which causes minimal damage to the skin which is exposed to laser radiation.

Yet another object of the invention is to provide a method of depilation which is simple to administer consistently to a large area without constant readjustment of the laser and at maximum efficiency so that only a single burst of energy will effectively vaporize the melanin in the hair follicle.

Yet another object of invention is to provide a method of hair shaft preparation to eliminate the need for an excess dosage of radiation which would be required if excess hair were present.

In summary, therefore, this invention is directed to a method of hair depilation and prevention of regrowth through substantial follicle destruction using a ruby-red laser. The treatment involves damaging selected hair follicles without significant injury to the surrounding skin.

These and other objects and advantages of the invention will be readily apparent in view of the following description of the above identified invention.

DESCRIPTION OF THE INVENTION

In using a laser, it is preferable to use the minimal amount of treatment required to achieve the objective. As with chemical epidermal treatments, overdosage can cause unwanted scarring or damage. Use of a Q-switched ruby laser, with a short pulse duration can produce the desired effect of depilation and eliminate hair regrowth. However, to avoid producing unwanted side-effects, such as scarring, the following method has been developed.

Using the process of selective photothermolysis, a laser wavelength is matched with the absorption spectrum of the melanin found at the base of the hair follicle. Melanin is a pigment which is concentrated at the base of the follicle, has an absorption spectrum that is highest in the ultraviolet range and gradually diminishes toward the infrared. These parameters are further narrowed because the depth of penetration of light is dependent on its wavelength and longer wavelengths are required to damage the hair follicle deep in the dermis.

Therefore, the depth of penetration can be selected through the selection of an appropriate wavelength and the damage at a particular depth is controlled by the energy applied. Of course, as higher energy levels are used, the depth of penetration will be increased through the generation and accumulation of heat through absorption. A careful balance of the laser parameters leads to destruction of the hair follicle without permanently destroying normal adjacent epidermal and dermal structures.

Figure 1:
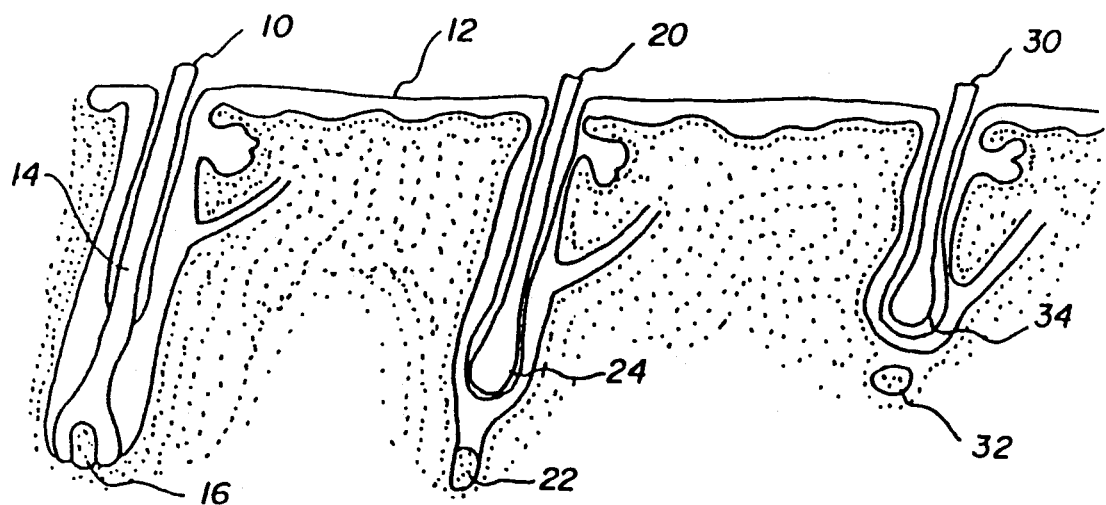
FIG. 1 is a cross-sectional view of three hair shafts showing the stages of the hair cycle.

FIG. 1 shows a hair shaft 10 which has been cut down to the near the surface of the skin 12. The shaft 10 extends down to the follicle 14 which at the anagen stage of the hair cycle joins the papilla 16. Destruction of the papilla 16 is necessary to prevent hair regrowth. After growing for about three years in the anagen stage, the hair shaft 10 enters the catagen stage represented by hair shaft 20 wherein the papilla 22 separates from the base of the follicle 24. The catagen stage lasts only a few weeks.

Hair shaft 30 represents the telogen stage of the hair cycle wherein the papilla 32 completely separates from the follicle 34 and forms a new secondary hair germ which will repeat the cycle. The telogen stage lasts about three months.

In order to assure sufficient injury to the papilla 32 at the telogen stage as well as the papilla 16 at the anagen stage, use of a laser with sufficient energy and depth of penetration is necessary to achieve sufficient melanosomal destruction.

Cutting of the hair shaft 10 down to the skin 12 provides two important functions of the treatment process.

First, the tip 18 of the hair shaft 10 allows the laser operator to position the laser substantially vertically over the hair follicle opening such that an optimum location for aiming the laser pulse to strike the papilla 16 is obtained. Second, the reduction of excess hair eliminates additional scattering of the radiant energy contained in the pulse.

Figure 2:
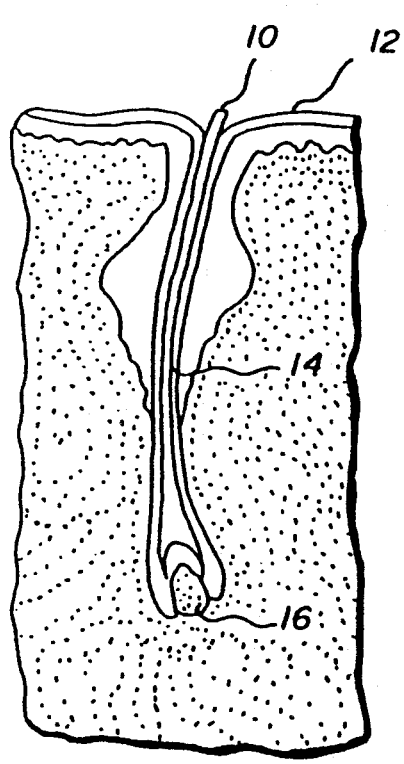
FIG. 2 is a cross-sectional view of a hair follicle after the top has been cut, but prior to application of laser pulse.

FIG. 2 shows an enlarged view of the hair shaft 10 prior to treatment, wherein the follicle 14 and papilla 16 are normal in appearance in the anagen stage.

Figure 3:
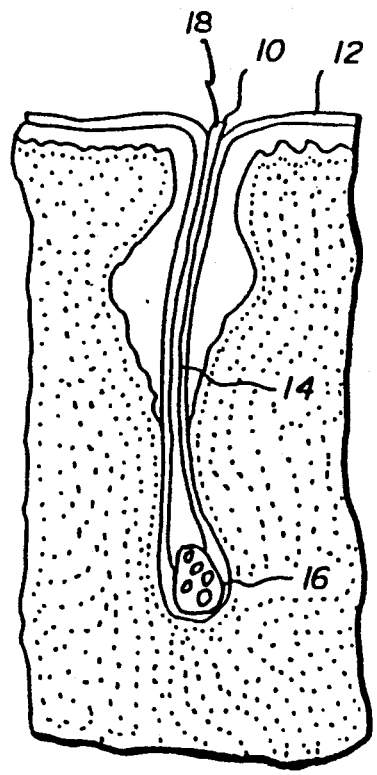
FIG. 3 is a cross-sectional view of the follicle of FIG. 2 after laser treatment, showing the damaged hair germ.

FIG. 3 show the treatment after the laser pulse has been applied to the follicle 14 and the resulting effect on the papilla 16.

Application of the laser pulse to the follicle and the papilla causes photothermolysis which provides melanosomal disruption, including vaporization of the melanin in the follicle 14 and papilla 16, as well as vacuolation, edema, gas bubbles and protein denaturation. When the pulse applied is of sufficient energy level, these effects seriously injure the hair follicle and papilla, thereby damaging the hair germ which causes hair regrowth.

The hair follicle 14 may extend into the reticular dermis up to 3 mm from the skin surface. In order to achieve the depth of penetration required to destroy the hair follicle 14, it has been found that a wavelength of about 694 nm, which is produced by the ruby red laser, is preferred. The ruby red laser tends to produce less severe dermal injury than lasers having longer wavelengths and better reticular dermal penetration than lasers having shorter wavelengths.

A Q-switched ruby red laser is used to deliver pulses at a wavelength of about 694 nm through an aperture plate held in contact with the skin. The port in the aperture plate ranges in size from the 3 mm up to 8 mm. The port of 3 mm is useful for treating individual hairs in the scalp. An opening of about 5 mm is necessary for treating single hairs over other areas of the body. Preferably, a port of 8 mm is used to treat areas of the body whereby up to 3 or 4 hairs may be treated at once.

The degree of follicular injury is dependent on the radiant exposure dose. Follicular damage is first observed at as low as 0.4 J/cm². At such a low dose, the hair may fall out of the skin, however, normal regrowth will soon occur. Scarring has been found to occur at about 10 J/cm². Preferably, the applied dosage should fall within the range of 0.4 J/cm² to 10.0 J/cm² and a dosage of 8.0 J/cm² is optimum.

In accordance with the process of selective photothermolysis, the pulse duration time should be shorter than the thermal relaxation time of the melanin. The thermal relaxation time is defined as the time it takes for a structure to cool to 50% of its peak temperature immediately after laser exposure. The calculated thermal relaxation time for melanosomes has been found to be approximately 1 microsecond. Therefore, selective damage to melanosomes will occur when they are exposed to submicrosecond laser pulses. A Q-switched ruby red laser delivering pulses in the range of 30 to 40 nanoseconds has been found to adequately disrupt the melanosomes in the hair follicle.

Different types of hair and hair color will require variations in the energy dosage to effect permanent hair removal. Generally, darker hair will induce more light scattering, therefore a higher dosage may be required. However, treatment of all hair containing melanin can be effectively treated by the Q-switched ruby red laser process.

While this invention has been described as having a preferred method, it is understood that it is capable of further modifications, uses and/or adaptions of the invention and following in general the principles of the invention and including such departures from the present disclosure have come within known or customary practice in the art to which the present invention pertains and as may be applied to essential features hereinbefore set forth, and fall within the scope of the invention or the limits of the claims appended hereto.

I claim:

1. A method of hair depilation, comprising the steps of:
   a) aligning a laser light applicator substantially vertically over a hair follicle opening, said applicator having an aperture of sufficient area to surround a hair follicle and overlie its papilla;
   b) applying through said aperture to the hair follicle a pulse of laser energy of a wavelength which is readily absorbed by the melanin of the papilla and having a radiant exposure dose of sufficient energy and duration to damage its papilla so that hair regrowth is prevented and scarring of the surrounding skin is avoided.

2. The method of hair depilation as set forth in claim 1, wherein:
   a) said laser light applicator includes an aperture diameter of at least three millimeters.

3. The method of hair depilation as set forth in claim 1, wherein:
   a) said applied radiant exposure dose is between 0.4 j/cm² and 10 j/cm² for a duration of less than one microsecond.

4. The method of hair depilation as set forth in claim 1, further including the step of:
   a) damaging the hair follicle by applying an energy pulse to specifically destroy melanosomes using a Q-switched ruby laser.

5. The method of hair depilation as set forth in claim 1, wherein:
   a) the duration of the laser energy pulse is in the range of thirty to forty nanoseconds.

6. The method of hair depilation as set forth in claim 1, wherein:
   a) the wavelength of the laser energy is closely matched to the absorption spectrum of the melanin.

* * * * *